Figure 1:
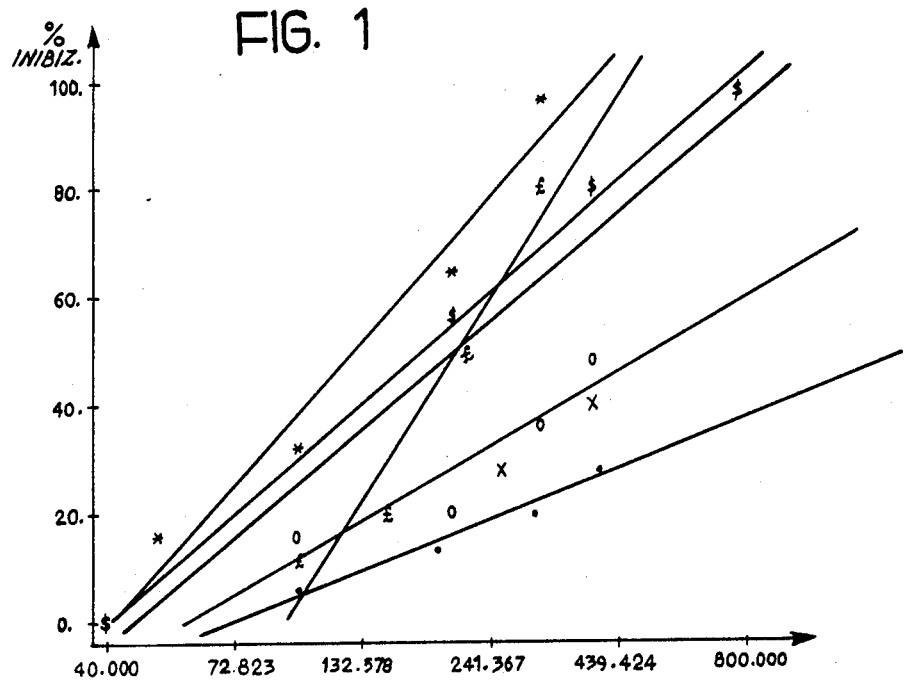

United States Patent [19]

Franzone et al.

[11] Patent Number: 4,868,186
[45] Date of Patent: Sep. 19, 1989

[54] THEOPHYLLINEMETHYLDITHIOLAN AND THEOPHYLLINEMETHYLDITHIANYL DERIVATIVES HAVING ANTIBRONCHOSPASTIC ANTITUSSIVE AND MUCOLYTIC ACTIVITY

[75] Inventors: José S. Franzone; Sergio De Vercelli, both of Torino, Italy

[73] Assignee: Istituto Biologico Chemioterapico ABC S.p.A., Torino, Japan

[21] Appl. No.: 137,694

[22] Filed: Dec. 24, 1987

[30] Foreign Application Priority Data

Dec. 24, 1986 [IT] Italy ............................... 67976-A/86

[51] Int. Cl.$^4$ ...................... A61K 31/52; C07D 473/08
[52] U.S. Cl. .................... 514/265; 544/267; 544/271; 544/272
[58] Field of Search ............... 544/267, 271; 514/265; 549/21, 33

[56] References Cited

U.S. PATENT DOCUMENTS

| | | | |
|---|---|---|---|
| 3,171,778 | 3/1965 | Slexak et al. | 549/21 X |
| 4,109,006 | 8/1978 | Johnson et al. | 549/21 X |
| 4,289,776 | 9/1981 | Mohler et al. | 514/263 |
| 4,309,553 | 1/1982 | Shepherd | 549/22 |
| 4,378,359 | 3/1983 | Chiodoni et al. | 514/265 X |
| 4,640,929 | 2/1987 | Mitsudera et al. | 549/21 X |
| 4,755,517 | 7/1988 | Bruns et al. | 514/263 |

FOREIGN PATENT DOCUMENTS

| | | | |
|---|---|---|---|
| 0039091 | 4/1981 | Japan | 544/267 |
| 0011981 | 1/1982 | Japan | 544/267 |
| 0134092 | 8/1983 | Japan | 544/267 |

OTHER PUBLICATIONS

Fieser, J. Am. Chem. Soc., vol. 76, pp. 1945–1947 (04/05/54).

Primary Examiner—Mukund J. Shah
Assistant Examiner—Diana G. Rivers
Attorney, Agent, or Firm—Sughrue, Mion, Zinn, Macpeak & Seas

[57] ABSTRACT

New derivatives of theophylline are described, which have the general formula:

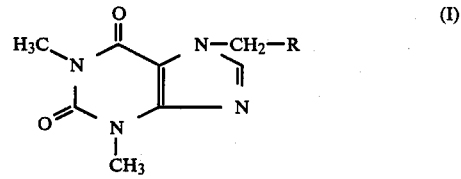

in which R is selected from the group consisting of 2'-(1'-oxy-1', 3'-dithiolanyl), 2'-(1', 3'-dithiolanyl) and 2'-(1',3'-dithianyl), possibly substituted in position 4'. The derivatives have high antibronchospastic, antitussive and mucolytic activities.

3 Claims, 1 Drawing Sheet

THEOPHYLLINEMETHYLDITHIOLAN AND THEOPHYLLINEMETHYLDITHIANYL DERIVATIVES HAVING ANTIBRONCHOSPASTIC ANTITUSSIVE AND MUCOLYTIC ACTIVITY

The present invention relates to new derivatives of theophylline substituted in position 7, which have antibronchospastic and antitussive activities and are usable in the treatment of disorders of the respiratory system.

U.S. Pat. No. 4,187,308 in the name of the Applicant describes the antibronchospastic and antitussive activity of the compound 7-[2'-(1'-3'-dioxolanyl)methyl]-theophylline and its use in the therapeutic treatment of bronchospasms, bronchial asthma and chronic bronchitis.

Italian Patent Application No. 21370-A/80, also in the name of the Applicant, describes a class of variously substituted theophyllinemethyldioxolan derivatives characterised by antitussive and antibronchospastic activity.

In continuing his research into the production of new theophylline derivatives with greater antibronchospastic and antitussive activity than known compounds, the Applicant has succeeded in identifying a new class of compounds.

Thus a subject of the present invention is constituted by new theophyllinemethyldithiolan and theophyllinemethyldithianyl derivatives having the general formula:

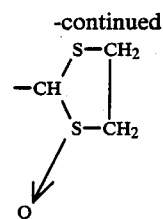

in which R is selected from the group consisting of

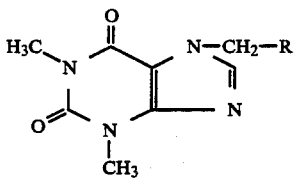

and

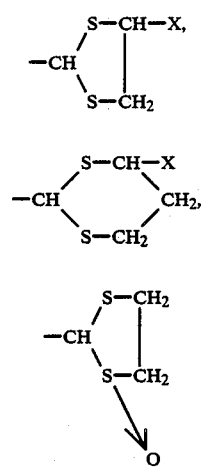

in which X is selected from the group consisting of H-, $-CH_2-NH_2$, $-CH_2-NHR_1$, $-CH_2-NHCOR_1$, $-CH_2OH$, $-CH_2OCOR_1$, $-CH_2OCOCOOH$, $-CH_2COOH$ and $-CH_2COOR_1$, in which $R_1$ is selected from the group consisting of methyl, ethyl and 2-oxyethyl, and their pharmaceutically acceptable salts.

Surprisingly, the compounds covered by the general formula defined above have mucolytic activity as well as antibronchospastic and antitussive activity.

Of the compounds indicated above, those preferred are ones in which X is hydrogen and, more particularly, the following:

Compound 1:
7-[2'-(1',3'-dithiolanyl)-methyl]-theophylline, melting point 125°–127° C.

Compound 2:
7-[2'-(1',3'-dithianyl)-methyl]-theophylline, melting point 151°–153° C.

Compound 3:
7-[2'-(1',3'-dithiolanyl)-methyl]-theophylline sulphoxide, melting point: 200°–202° C. and Compound 4:
7-[2'-(1',3'-dithiolanyl)-methyl]-theophylline sulphoxide, the diastereoisomer of compound 3, melting point 201°–203° C.

In particular, the aforementioned compounds (1)–(4) do not cause side effects or habituation at therapeutic doses, even with prolonged treatment and have negligible toxicity.

All these compounds have shown bronchomyorelaxing activity and simultaneous mucolytic action; Compound (1) is the one which has the most favourable therapeutic index. The derivatives in which X is other than hydrogen and is selected from the aforementioned group with X substituents of a hydrophilic nature, are precursors of the compounds (1)–(4) which are able to liberate these compounds as a result of simple metabolic transformations, limited to hydrolysis.

A further subject of the present invention is constituted by the methods for the preparation of the aforementioned compounds.

In particular, the method for the preparation of the derivatives of formula (I), in which R is constituted by the radicals (II) and (III) given above, includes the steps of reacting 7-theophylline-acetaldehyde with a dithiol selected from the group consisting of ethanedithiol and 1,3-propanedithiol, substituted with an X radical selected from the aforementioned group.

The synthesis is preferably carried out in ethereal solution at a temperature no higher than 75° C. in the presence of acid catalysts of the Lewis acid type, anhydrous halogen hydracids, or sulphuric acid. The solvent is removed and the product of the synthesis is then purified preferably in a chloroform solution, by basic washing and subsequent chromotography on silica gel.

The general method for the synthesis of the compounds (3) and (4) comprises the reaction of the dithiolan derivative with hydrogen peroxide. The dithiolan derivative is preferably dissolved in glacial acetic acid and the reaction is carried out with hydrogen peroxide preferably 35% hydrogen peroxide at room temperature. Upon completion of the reaction, the product is precipitated with ethyl ether and the compound obtained is collected in a Buckner funnel. The diastereoisomeric derivatives (3) and (4) are separated and purified in a column of silica. In the preparative tests carried out, the IR, NMR and mass spectra confirmed the structures shown above.

EXAMPLE 1

Preparation of compound (1):
7-[2'-(1',3'-dithiolanyl)methyl]-theophylline 10 g of 7-theophylline-acetaldehyde (molecular weight 222) are dissolved in 350 ml of anhydrous dioxan and heated to a temperature of between 60° and 70° C. 10 ml of ethane-1,2-dithiol and 12.5 ml of boron trifluoride etherate are added. The mixture is left to react for 5 hours, while the above temperature is maintained. The dioxan is removed under vacuum and the residue is taken up with 300 ml of chloroform. The chloroform solution is washed with a 5% NaOH solution and then with a saturated NaCl solution. The solvent is removed and the product is purified in a column of silica with a $CH_2Cl_2$/ethanol (99:1) eluent.

Yield: 70%. Recrystallised from methanol, the compound has a melting point of 125°–127° C.

The mass, IR and NMR spectra confirm the structure of compound (1).

The compounds according to the invention and their pharmaceutically-acceptable salts may be administered in conventional pharmaceutical forms, such as tablets, capsules, suspensions, granules, and suppositories, together with conventional excipients, carriers, colouring agents and sweeteners, particularly for the treatment of bronchospasms, bronchial asthma, and chronic obstructive bronchitis associated with mucous and spastic coughing.

By way of example, the compositions of preferred pharmaceutical forms are shown below.

Pharmaceutical forms

Tables and capsules having the following composition:

| | |
|---|---|
| *Dithiolan | 0.200 g |
| mannitol | 0.070 g |
| microcrystalline cellulose | 0.052 g |
| colloidal silica | 0.026 g |
| talc | 0.024 g |
| P.V.P. | 0.020 g |
| magnesium stearate | 0.008 g |

*The term diothiolan refers to compound (1): 7-[2'-(1',3'-dithiolanyl)-methyl]-theophylline.

400 mg tables and capsules

| | |
|---|---|
| *Dithiolan | 0.400 g |
| mannitol | 0.100 g |
| microcrystalline cellulose | 0.052 g |
| colloidal silica | 0.026 g |
| talc | 0.050 g |
| P.V.P. | 0.030 g |
| magnesium stearate | 0.010 g |

500 mg retarded tablets with the following composition:

| | |
|---|---|
| *Dithiolan | 500 mg |
| sucrose | 240 mg |
| maize starch | 50 mg |
| magnesium stearate | 10 mg |
| microcrystalline cellulose | 100 mg |
| diffulac | 100 mg |

2.5% oral suspension
The suspension per 100 g:

| | |
|---|---|
| *Dithiolan | 2.50 g |
| sorbitol, 70% | 50.00 g |
| levilite | 4.00 g |
| emulsional | 1.20 g |
| soluble extract of orange | 1.00 g |
| methyl p-hydroxybenzoate | 0.13 g |
| distilled water qs. up to | 100 g | effervescent granules
each packet contains:

| | neonatalogical use | paediatric use |
|---|---|---|
| *Dithiolan | 0.050 g | 0.100 g |
| lyophylised citrus fruit | 0.5 g | 1 g |
| fructose | 1.25 g | 2.5 g |
| citric acid | 0.25 g | 0.5 g |
| sodium bicarbonate | 0.35 g | 0.7 g | suppositories for paediatric use

| | |
|---|---|
| *Dithiolan | 200 mg |
| semisynthetic glycerides qs. up to | 1.5 g | suppositories for adult use

| | |
|---|---|
| *Dithiolan | 400 mg |
| semisynthetic glycerides qs. up to | 2.5 g |

Pharmacological activity

The pharmacological activity of the preferred compounds according to the invention was tested in comparison with the activity of known compounds such as doxophylline (7-[2'-(1',3'-dioxolanyl)-methyl]-theophylline) and aminophylline by means of a series of tests in vitro and in vivo.

Tests in vitro (a) Activity of compounds (1), (2), (3), (4) according to the invention, doxophylline and aminophylline on completely-removed guinea-pig tracheas.

Thirty white guinea-pigs were used, from which the tracheas were removed, after they had been killed by ethereal anaesthesia.

The tracheas were placed in a 50 ml bath of Krebs solution, suitably oxygenated and thermoregulated at a temperature of 37° C.

The lower end of the trachea was closed while the upper end was connected to a polythene tube connected to a transducer for measuring volume differences connected to a polygraph, according to D. Jamieson's method 1962, Brit. J. Pharmacol. and Chemiotherapy, 19, 286, partially modified.

Both the trachea and the polythene tube were filled with Krebs solution. The responses of the tracheas thus prepared to acetylcholine and histamine were investigated before and after the addition of the product to the bath. The results obtained are shown in Table I and in FIG. 1.

TABLE No. I

Effect of compounds 1, 2, 3, 4, doxophylline and aminophylline on the constrictive action of histamine di-hydrochloride ($5.10^{-6}$ g/ml) on completely removed guinea-pig tracheas.

| Substance | concentration ($10^{-6}$ g/ml) | % inhibition | $ED_{50}$ ($10^{-6}$ g/ml) |
|---|---|---|---|
| COMPOUND 1 | 50 | −17.2 | |
| | 100 | −32.5 | |
| | 200 | −62.5 | 126.1 |
| | 300 | −95.0 | |
| COMPOUND 2 | 100 | −12.0 | |
| | 200 | −18.5 | |
| | 250 | −26.5 | 837.1 |
| | 400 | −38.5 | |
| COMPOUND 3 | 100 | −14.5 | |
| | 200 | −21.5 | |
| | 300 | −35.4 | 530.0 |
| | 400 | −47.5 | |
| COMPOUND 4 | 100 | −7.5 | |
| | 200 | −12.5 | |
| | 300 | −20.4 | 2241.8 |
| | 400 | −27.8 | |
| DOXOPHYLLINE | 40 | 0 | |
| | 200 | −54 | |
| | 400 | −78 | 175.0 |
| | 800 | −100 | |
| AMINOPHYLLINE | 100 | −10.9 | |
| | 150 | −18.7 | |
| | 200 | −46.15 | 206.1 |
| | 300 | −79.4 | |

EFFECT OF COMPOUNDS 1, 2, 3, 4, DOXOPHYLLINE AND AMINOPHYLLINE ON THE CONSTRICTIVE ACTION OF HISTAMINE DI-HYDROCHLORIDE (5 microg/ml) ON COMPLETELY-REMOVED GUINEA-PIG TRACHEAS (see FIG. 1).

*—* COMPOUND 1
ED 50 = 126.119
C.L. 95% = 52.3643–303.757
C.L. 99% = 25.1208–633.179
X—X COMPOUND 2
ED 50 = 837.153
C.L. 95% = 268.149–2613.56
C.L. 99% = 103.565–6767
O—O COMPOUND 3
ED 50 = 530
C.L. 95% = 164.287–1524.25
C.L. 99% = 76.2289–3684.96
S—S DOXOPHYLINE
ED 50 = 177.161
C.L. 95% = 165.656–189.465
C.L. 99% = 156.616–200.401
— AMINOPHYLLINE
ED 50 = 206.105
C.L. 95% = 116.876–363.458
C.L. 99% = 72.7532–583.883
●—● COMPOUND 4
ED 50 = 2241.84
C.L. 95% = 424.242–11846.7
C.L. 99% = 105.549–47616.2
C.L. = Confidence Level The tests in vivo were only conducted on compound (1), which, on the basis of the results obtained in vitro, was the most active.

(a) Comparative activity of compound (1) (7-[2'-1',3'-dithiolanyl)-methyl]-theophylline), doxophylline and aminophylline on bronchospasm by acetylcholine chloride (0.075 mg/kg i.v.), in guinea-pigs.

For these tests, Konzett and Roesler's method (1940) Arch. Exp. Path. Pharmak, 191, 71, was used with some of the modifications of Collier H.O.J. (1960), Brit. J. Pharmcol. 15, 290.

Male guinea-pigs weighing 300–450 g were used under urethane anaesthesia (lg/kg i.p.).

The animals were suitably prepared by insertion of a cannula in the jugular vein for intravenous administrations while the trachea was connected to an artificial respiration pump (Palmer) adapted for small animals, which was operated at a frequency of approximately 70 insufflations per minute. The pneumogram was recorded by means of a transducer on a polygraph (Battaglia-Rangoni).

Bronchospasm was induced in the guinea-pig by means of intravenous injection of acetylcholine at a dose of 0.075 mg/kg i.v. After two equal responses to the acetylcholine, the drugs under study were administered i.v.

Figure 2:
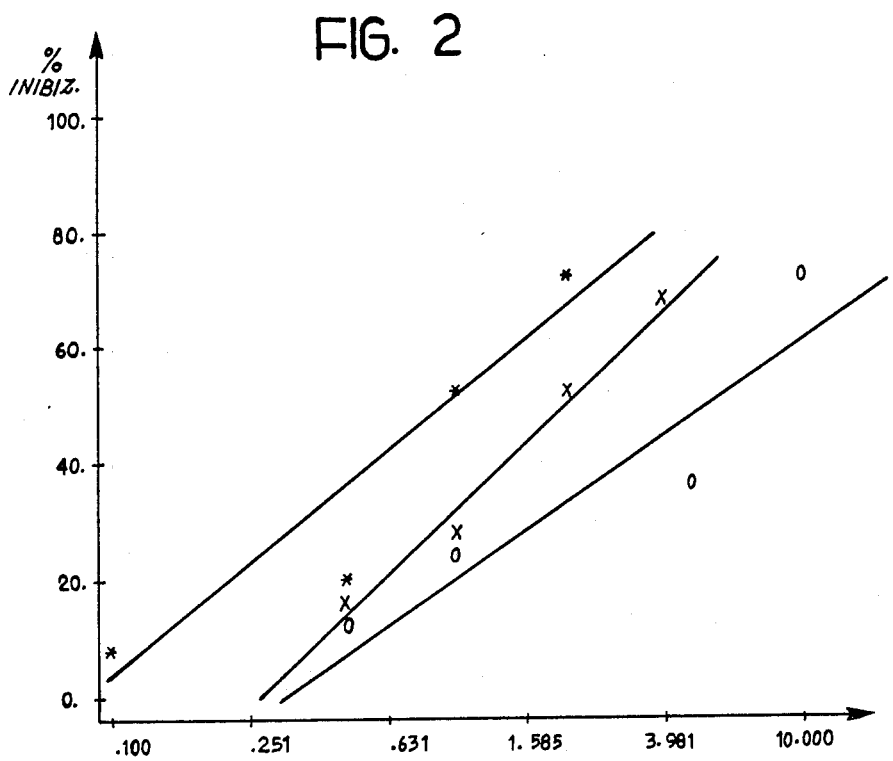

The results obtained are shown in Table II and FIG. 2.

TABLE II

Inhibiting effect of compound 1 (2-(7'-theophylline-methyl)-1,3-dithiolan), doxophylline, (2-(7'-theophylline-methyl)-1,3-dioxolan) and aminophylline on bronchospasm by acetylcholine chloride (0.075 mg/kg i.v.) in guinea-pigs.

| Substance | No. of animals | Dose mg/kg i.v. | % Variation in endobronchial pressure after administration of acetylcholine chloride (0,075 mg/kg i.v.) $\overline{M} \pm SE$ | % inhibition vs. controls | ED50 mg/kg i.v. |
|---|---|---|---|---|---|
| CONTROLS | 20 | — | 181.4 ± 21.2 | — | — |
| | 6 | 0.1 | 166.0 ± 22.4 | −8.5 | |
| | 6 | 0.5 | 145.1 ± 18.7 | −20.0 | |
| COMPOUND 1 | 6 | 1 | 87.1 ± 15.2 | −52.0 | 0.99 |

TABLE II-continued

Inhibiting effect of compound 1 (2-(7'-theophylline-methyl)-1,3-dithiolan), doxophylline, (2-(7'-theophylline-methyl)-1,3-dioxolan) and aminophylline on bronchospasm by acetylcholine chloride (0.075 mg/kg i.v.) in guinea-pigs.

| Substance | No. of animals | Dose mg/kg i.v. | % Variation in endobronchial pressure after administration of acetylcholine chloride (0,075 mg/kg i.v.) $\overline{M} \pm SE$ | % inhibition vs. controls | ED50 mg/kg i.v. |
|---|---|---|---|---|---|
| | 6 | 2 | 51.7 ± 6.5 | −71.5 | |
| | 6 | 0.5 | 153.8 ± 18.4 | −15.2 | |
| | 6 | 1 | 133.3 ± 14.8 | −26.5 | |
| DOXOPHYLLINE | 6 | 2 | 88.5 ± 11.3 | −51.2 | |
| | 6 | 4 | 56.4 ± 8.8 | −68.9 | |
| | 6 | 0.5 | 158.7 ± 24.6 | −12.5 | |
| | 6 | 1 | 135.7 ± 21.2 | −25.2 | |
| AMINOPHYLLINE | 6 | 5 | 117.0 ± 17.4 | −35.5 | 4.97 |
| | 6 | 10 | 49.9 ± 10.2 | −72.5 | |

EFFECT OF COMPOUND 1, DOXOPHYLLINE AND AMINOPHYLLINE ON BRONCHOSPASM, BY ACETYLCHOLINE CHLORIDE (0.075 mg/kg i.v.) IN GUINEA-PIGS (FIG. 2).
*—* COMPOUND 1
ED 50 = .996124
C.L. 95% = .104729–9.47454
C.L. 99% = 1.59445E-02 - 62.2324
X—X DOXOPHYLLINE
ED50 = 2.01949
C.L. 95% = 1.18433–3.44359
C.L. 99% =.758225–5.37881
O—O AMINOPHYLLINE
ED50 = 4.97479
C.L. 95% = .300261–82.4231
C.L. 99% = 2.87493E-02–860.839
C.L. = Confidence Level The results given in the Table show that the antibronchospastic effect of compound (1), 7-[2'-(1',3'-dithiolanyl)-methyl)-theophylline is approximately twice that of doxophylline and approximately five times that of aminophylline.

(b) Mucolytic activity of compound 1, doxophylline and bromohexyne hydrochloride For these tests the method described by Perry, W. F., Boyd, E. M., J. Pharmacol., 1941, 73, 65 and suitably modified by us was used.

New Zealand-type, male, white rabbits weighing 2.8–3.5 kg. were used.

Pre-operative preparation consisted of treatment with 9 mg/kg i.m. of a non-stupefying central analgesic (tilidine) and local anaesthesia in the tracheal region with xylocaine (0.9 mg/kg - 1% solution). The surgical operation commenced 15–20 minutes after the pharmacological pre-treatment.

The trachea was exposed and a hole approximately 5–6 mm in diameter was made in its ventral side. The trachea was then introduced into the lower arm of a three-way polypropylene cannula, which had been cut suitably, longitudinally so as to connect the hole made in the trachea with the aperture of the third arm (vertical) of the cannula, and thus put it into communication with the outside.

Thus, the cannula surrounded the outside of the trachea and was fixed "in loco" with sterile surgical silk thread.

A polypropylene container was attached to the vertical arm of the cannula for collecting the mucous (capacity approximately 2 ml), and the wound was then sutured.

The tracheal mucous was collected for four hours before the oral administration of the substance under test and for four hours after the treatment.

The results obtained are shown in Table III below.

From these, it is clear that the compound (1) has a dose-related mucolytic activity: at a dose of 100 mg/kg it was more active than bromohexyne hydrochloride at a dose of 400 mg/kg; doxophylline, however, showed no mucolytic activity.

TABLE NO. III

Mucoproduction in rabbits before and after treatment with compound 1 administered at various doses, doxophylline N—acetylcysteine and bromohexyne hydrochloride.

| Substance | No. of animals | Dose mg/kg os | Mucoproduction (mg/h) $M \pm SD$ 4–0 h (before the treatment) | 0–4 h (after the treatment) | % Variation with respect to its own base | Statistical significance with respect to its own base |
|---|---|---|---|---|---|---|
| CONTROL | 10 | — | 29.5 ± 8.32 | 31.25 ± 5.93 | +5.93 | N.S. |
| | 10 | 10 | 30.6 ± 9.43 | 34.87 ± 10.25 | +13.95 | N.S. |
| COMPOUND 1 | 10 | 30 | 27.2 ± 5.22 | 34.53 ± 4.16 | +26.95 | P ≦ 0.05 |
| | 10 | 100 | 29.7 ± 4.95 | 46.71 ± 8.82 | +57.27 | P ≦ 0.01 |
| DOXOPHYLLINE | 10 | 100 | 29.8 ± 5.80 | 32.10 ± 8.26 | +7.71 | N.S. |
| BROMOHEXYNE | 10 | 400 | 28.9 ± 7.82 | 39.01 ± 4.34 | +34.98 | P ≦ 0.05 |
| N—acetylcysteine | 10 | 400 | 27.7 ± 5.50 | 32.19 ± 3.89 | +16.21 | P ≦ 0.05 |

Determination of acute toxicity

Determination of the acute oral toxicity of compound (1) was carried out both in mice and in rats, with the use of doxophylline and aminophylline as reference products.

The products were administered in a 0.5% aqueous suspension of carboxymethylcellulose at a concentration of 1 ml/100 g of body weight.

After treatment with the respective drugs, the animals were observed for 20 consecutive days, their general condition, behaviour and mortality being noted.

The $LD_{50}$ values were calculated by Litchfield and Wilcoxon's statistical method (1949) J. Pharmacol. Exp. Therap. 96, 99.

TABLE NO. IV $LD_{50}$ values and fiduciary limits obtained in mice and rats for compound 1 (2-(7′ theophylline-methyl)-1,3-dithiolan), for doxophylline (2-(7′-theophylline-methyl)-1,3-dioxolan) and aminophylline administered orally.

| Substance | $LD_{50}$ (mg/Kg os) | |
|---|---|---|
| | MOUSE | RAT |
| COMPOUND 1 | 1510 (1403–1608) | 1835 (1748–1941) |
| DOXOPHYLLINE | 870 (778–960) | 965 (885–1055) |
| AMINOPHYLLINE | 540 (442–651) | 585 (496–682) |

We claim:

1. 7-[2′-(1′,3′-dithiolanyl)-methyl]-theophylline, or a pharmaceutically acceptable salt thereof.

2. Pharmaceutical composition having antibronchospastic, antitussive and mucolytic activity comprising an antibronchospastic, antitussive and mucolytic effective amount of 7-[2′-(1′,3′-dithiolanyl)-methyl]-theophylline, or a pharmaceutically acceptable salt thereof, and a pharmaceutically acceptable carrier.

3. A method for treating a patient having bronchospasm, bronchioasthma or chronic obstructive bronchitis, which comprises administering to said patient an antibronchospastic, antitussive and mucolytic effective amount of 7-[2′-(1′,3′-dithiolanyl)-methyl]-theophylline, or a pharmaceutically acceptable salt thereof.

* * * * *